(12) United States Patent
Marks et al.

(10) Patent No.: US 7,737,240 B2
(45) Date of Patent: Jun. 15, 2010

(54) HYDROGEL FUNCTIONALIZED WITH A POLYMERIZABLE MOIETY AND THEIR USES AS BIOSENSORS OR BIOREACTORS

(75) Inventors: Robert Marks, Omer (IL); Serge Cosnier, Crolles (FR); Boris Polyak, Philadelphia, PA (US); Elena Rodica Ionescu, Judetul Ilfov (RO); Khalil Abu-Rabeah, Beer-Sheva (IL)

(73) Assignees: Universite Joseph Fourier-Grenoble 1, St. Martin d'Heres (FR); Ben-Gurion University of the Negev Research and Development Authority, Beer-Sheva (IL)

( * ) Notice: Subject to any disclaimer, the term of this patent is extended or adjusted under 35 U.S.C. 154(b) by 0 days.

(21) Appl. No.: 12/041,570

(22) Filed: Mar. 3, 2008

(65) Prior Publication Data

US 2008/0242738 A1    Oct. 2, 2008

Related U.S. Application Data

(63) Continuation of application No. PCT/EP2005/054846, filed on Sep. 27, 2005.

(51) Int. Cl.
| | | |
|---|---|---|
| C08F 251/00 | (2006.01) | |
| A61K 47/48 | (2006.01) | |
| A61K 9/14 | (2006.01) | |
| C12M 1/00 | (2006.01) | |
| C12N 9/00 | (2006.01) | |
| C12N 11/00 | (2006.01) | |
| C25B 9/00 | (2006.01) | |
| C25B 11/00 | (2006.01) | |
| C25B 13/00 | (2006.01) | |
| G01N 1/00 | (2006.01) | |
| G01N 27/26 | (2006.01) | |
| G01N 31/00 | (2006.01) | |
| G01N 33/50 | (2006.01) | |
| G01N 33/487 | (2006.01) | |

(52) U.S. Cl. .............. 527/312; 527/300; 525/54.2; 424/488; 204/403.1

(58) Field of Classification Search ............... 525/54.2; 527/300, 312; 424/488; 204/403.1
See application file for complete search history.

(56) References Cited

U.S. PATENT DOCUMENTS

| 5,183,872 | A | * | 2/1993 | Heidel et al. ............... 527/300 |
| 5,243,008 | A | * | 9/1993 | Ahmed et al. .............. 527/309 |
| 5,690,961 | A | * | 11/1997 | Nguyen ..................... 424/488 |
| 6,013,774 | A | * | 1/2000 | Meister et al. ............. 530/507 |
| 6,586,493 | B1 | * | 7/2003 | Massia et al. ............... 522/87 |
| 6,602,975 | B2 | * | 8/2003 | Hubbell et al. ............. 528/354 |
| 6,630,460 | B2 | * | 10/2003 | Koulik ....................... 514/56 |

(Continued)

OTHER PUBLICATIONS

Cosnier et al. Analytica Chimica Acta 453 (2002) 71-79.*

(Continued)

*Primary Examiner*—Mark Eashoo
*Assistant Examiner*—Liam J Heincer
(74) *Attorney, Agent, or Firm*—Baker Donelson Bearman, Caldwell & Berkowitz, PC

(57) ABSTRACT

The present invention relates to a new hydrogel functionalized with a polymerizable moiety, the polymerized hydrogels, films and gels comprising the same and their use for cells, proteins, DNA or other molecules encapsulation, including use as biosensors or bioreactors.

29 Claims, 1 Drawing Sheet

U.S. PATENT DOCUMENTS

| | | | | |
|---|---|---|---|---|
| 6,660,484 | B2* | 12/2003 | Charych et al. | 435/7.1 |
| 6,703,444 | B2* | 3/2004 | Zhao et al. | 525/61 |
| 7,057,019 | B2* | 6/2006 | Pathak | 530/362 |
| 2003/0008971 | A1* | 1/2003 | Won et al. | 525/54.2 |
| 2003/0099684 | A1* | 5/2003 | Domb | 424/426 |
| 2004/0029241 | A1* | 2/2004 | Hahn et al. | 435/174 |
| 2004/0185564 | A1* | 9/2004 | Tang et al. | 435/455 |
| 2004/0202625 | A1* | 10/2004 | Daniloff et al. | 424/63 |
| 2005/0042612 | A1* | 2/2005 | Hubbard et al. | 435/6 |
| 2005/0069572 | A1* | 3/2005 | Williams et al. | 424/426 |
| 2005/0108832 | A1* | 5/2005 | Torri et al. | 8/181 |
| 2005/0187146 | A1* | 8/2005 | Helmus et al. | 514/8 |
| 2005/0265959 | A1* | 12/2005 | Calabro et al. | 424/78.27 |
| 2006/0014163 | A1* | 1/2006 | Dervan et al. | 435/6 |
| 2006/0057098 | A1* | 3/2006 | Sato | 424/78.17 |
| 2006/0128918 | A1* | 6/2006 | Chu et al. | 527/300 |
| 2006/0142476 | A1* | 6/2006 | Weerawarna | 525/54.1 |
| 2006/0148923 | A1* | 7/2006 | Ashman et al. | 522/7 |
| 2006/0188465 | A1* | 8/2006 | Perrier et al. | 424/70.13 |
| 2006/0251613 | A1* | 11/2006 | Zhang et al. | 424/78.27 |
| 2006/0254738 | A1* | 11/2006 | Anderson et al. | 162/175 |
| 2007/0026070 | A1* | 2/2007 | Vonwiller et al. | 424/486 |
| 2007/0031503 | A1* | 2/2007 | Hirakura et al. | 424/490 |
| 2007/0196426 | A1* | 8/2007 | Hermitte et al. | 424/426 |
| 2008/0058469 | A1* | 3/2008 | Abe et al. | 525/54.31 |

OTHER PUBLICATIONS

Smeds K. A. et al: "Photocrosslinkable Polysaccharides for In Situ Hydrogel Formation," Journal of Biomedical Materials Research, Wiley, NY NY, US, vol. 54, No. 1, Jan. 2001, pp. 115-121, XP008018719, ISSN: 0021-9304; abstract; p. 117, left-hand column.

Yang S. et al.: "Chitaline Materials" Soluble Chitosan -Polyaniline Copolymers and their Conductive Doped Forms, Synthetic Metals, vol. 32, 1989, pp. 191-200, XP002380948; p. 193, paragraph 2; figure 1.

Tokura S. et al: "Preparation of Alcohol-Soluble Chitin Derivatives and Radical Induction by Photo-Irradiation" Carbohydrate Polymers, Applied Science Publishers, Ltd. Barking, GB, vol. 13, No. 4, Jan. 1990, pp. 363-374, XP000133731, ISSN: 0144-8617; p. 365, par. 3; p. 370, par 3.

Zhang M et al: "Novel N-unsaturated fatty acyl and N-trimethylacetyl derivaties of chitosan," Carbohydrate Polymers, Applied Science Publishers, Ltd. Barking, GB, vol. 26, No. 3, 1995, p. 205-209, XP004034478, ISSN: 0144-8617; p. 206, left-hand column;abstract.

Gandini A. et al: "Furan-polyether-modified chitosans as photosensitive polymer electrolytes," Polymer, Elsevier Science Publishers B.V., GB, vol. 44, No. 25, Dec. 2003, p. 7565-7572, XP004471086, ISSN: 0032-3861; p. 7566, right-hand column.

Cosnier S. et al: "Enhancement of Biosensor Sensitivity in Aqueous and Organic Solvents Using a Combination of Poly(Pyrrole-Ammonium) and Poly(Pyrrole-Lactobionamide) Films as Host Matrices," Journal of Electroanalytical Chemistry, Lausanne, Ch, vol. 449, No. ½, 1998, pp. 165-171, XP000913952, ISSN: 0368-1874; abstract; figure 1.

International Search Report, PCT/EP2005/054846, dated Jun. 1, 2006.

Cosnier, Serge. "Biosensors based on electropolymerized films: new trends", Anal Bioanal Chem. 2003, 377, pp. 507-520.

Vadgama, Pankaj, et al., "Biosensors: Recent Trends A Review", Analyst. 1992, 117, pp. 1657-1670.

Torres, Luis G., et al., "Production and characterization of Ca-alginate biocatalyst for removal of phenol and chlorophenols from wastewaters" Biochem. 1998, vol. 33, No. 6, pp. 625-634.

Kierstan, M., et al., "The immobilization of microbial cells, subcellular organelles, and enzymes in calcium alginate gels" Biotech. Bioeng. 2000, vol. 67, pp. 726-736.

Gombotz, Wayne R., et al., "Protein release from alginate matrices" Adv.Drug.Deliv.Rev.1998, vol. 31, pp. 267-285.

Cosnier, Serge, et al., "Biotinylated alginate immobilization matrix in the construction of an amperometric biosensor: application for the determination of glucose" Analytica Chim.Acta. 2002, vol. 453, pp. 71-79.

Smidsord, Olav, et al., "Alginate as immobilization matrix for cells", TIBTECH. 1990, vol. 8, pp. 71-78.

Ortega, N. et al., "Optimisation of B-glucosidase entrapment in alginate and polyacrylamide gels", Bioresour. Technol. 1998, vol. 64, pp. 105-111.

Martinsen, A. et al., "Alginate as immobilization material: I. Correlation between chemical and physical properties of alginate gel beads", Biotechnol.Bioeng. 1989, vol. 33, pp. 79-89.

Blandino, Ana, et al., "Glucose oxidase release from calcium alginate gel capsules", Enzyme.Microb. Technol. 2000, vol. 27, pp. 319-324.

Levy, M.-C, et al., "Coating alginate beads with cross-linked biopolymers: a novel method based on a transacylation reaction", J. Microencapsulation. 1996, vol. 13, No. 2, pp. 169-183.

Sartori, Celine, et al.,"Determination of the cation content of alginate thin films by FTi.r. spectroscopy", Polymer. 1997, vol. 38, No. 1, pp. 43-51.

Khorana, H.G., "The Chemistry of carbodiimides", Chem. Rev. 1953, vol. 53, pp. 145-166.

Detar, Delos F. et al., "Reactions of carbodiimides III. The Reactions of carbodiimides with peptide acids", J.Am.Chem.Soc. 1966, vol. 88, pp. 1024-1030.

Anderson, George W., et al., "The use of esters of N-hydroxysuccinimide in peptide synthesis", J.Am.Chem.Soc. 1964, vol. 86, pp. 1839-1842.

Staros, James V., "N-hydrozysulfosuccinimide active esters: Bis(N-hydrozysulfosuccinimide) esters of two dicarboxylic acids are hydrophilic, membrane-impermeant, protein cross-linkers", Biochemistry. 1982, vol. 21, pp. 3950-3955.

Polyak, Boris, et al. "Synthesis and characterization of a biotin-alginate conjugate and its application in a biosensor construction", Biomacromolecules. 2004, vol. 5, pp. 389-396.

Rowley, Jon A., et al., "Alginate hydrogels as synthetic extracellular matrix materials", Biomaterials. 1999, vol. 20, pp. 45-53.

Turquois, Tristan, et al., "Determination of the absolute molecular weight averages and molecular weight distributions of alginates used as ice cream stabilizers by using multiangle laser light scattering measurements", J.Agric.Food.Chem. 2000, vol. 48, pp. 5455-5458.

Debye, P. "Light scattering in solutions", J.Appl.Phys. 1943, vol. 15, pp. 338-342.

Aubree-Lecat, Anne, et al., "Direct electrochemical determination of glucose oxidase in biological samples", Anal. Biochem. 1989, vol. 178, pp. 427-430.

Schacht, E., et al., "The use of gelatin and alginate for the immobilization of bioactive agents", Encapsulation and Controlled Release. Royal Society of Chemistry, Cambridge, 1993, pp. 18-34.

* cited by examiner

HYDROGEL FUNCTIONALIZED WITH A POLYMERIZABLE MOIETY AND THEIR USES AS BIOSENSORS OR BIOREACTORS

CROSS-REFERENCE TO RELATED APPLICATIONS

This application is a continuation of International Application Number PCT/EP2005/054846, filed Sep. 27, 2005, the entire disclosure of which is incorporated herein by reference.

The present invention relates to a new hydrogel functionalized with a polymerizable moiety, the polymerized hydrogels, films and gels comprising the same and their use for cells, proteins, DNA or other molecules encapsulation, including use as biosensors or bioreactors.

Biosensors enable direct, sensitive, and rapid analysis of biological and chemical species and hence are used in many areas of health care and life science, ranging from uncovering and diagnosing disease, to the discovery and screening of new drugs and molecules (Cosnier, S. *Anal. Bioanal. Chem.* 2003, 377, 507-520; Maite, S. Francisco, A. *J. Chemical. Reviews.* 2003, 104, 3239-3265; Vagdama, P. Crump, P. *Analyst.* 1992, 117, 1657)

Biosensor devices couple an immobilized biospecific recognition entity to the surface of a transducer, which 'transduces' a molecular recognition event into a measurable electrical signal, pinpointing to the presence of the target molecule.

Hydrogel matrices have been widely used to construct biosensors such as the promising hydrogel alginate, which belong to a family of copolymers containing 1,4-linked β-D-mannuronic, and α-L-guluronic acid residues that vary in both proportions and sequential arrangements (Torres, L. G. Sanches-de-la-vega, N. A. process *Biochem.* 1998, 33, 625; Kierstan, M. Bucke, C. *Biotech. Bioeng.* 2000, 67, 726; Gombotz, W. R. Wee, S. F. *Adv. Drug Delv. Rev.* 1998, 31, 267; Cosnier, S. Novoa, A. Mousty, C. Marks, R. S. *Analytica Chim Acta.* 2002, 453, 71-79).

Gels form thereof spontaneously in the presence of divalent ions like calcium in a single-step process undergone at very mild conditions. The large technical success in their entrapment and encapsulation is due to the gentle environment they provide the trapped material, as well as, the existence of high porosity, due to the open lattice structure in the gel. This allows for high diffusion rates within the whole gel structure and facilitates exchanges with aqueous solution. However, precisely due to this high porosity, macromolecules such as enzymes will leak out into the aqueous solution, thus, limiting the use of such a matrix to mostly whole cells or cell organelles (Smidsord, O. Skajak-Barak, G. *TIBTECH.* 1990, 8, 71; Oretega, N. Busto, M. D. PerazMateos, M. *Bioresour. Technol.* 1998, 64, 105; Martinsen, A. Skajak, G. Smidsord, O. *Biotechnol. Bioeng,* 1989, 33, 79; Blandino, A. Mcias, M. Cantero, D. *Enzyme. Microb. Technol.* 2000, 27, 319).

Several procedures to stabilize alginate gels and reduce their porosity in order to provide them with the property of controlled-release have been proposed. The most frequently used methods are polycationic coating (Schacht, S. Vandichel, J. C. Encapsulation and Controlled Release, Royal Society of Chemistry, Cambridge, 1993, 18-34) and covalent cross-linking (Levy, M. C; Edward-Levy, F. *J. Microencapsulation.* 1996, 13, 169), still not satisfactory.

The present invention concerns thus a new functionalized hydrogel where an hydrogel backbone and a polymer are bonded with one or more covalent bonds, the polymer being formed in situ by polymerization of a functionalized hydrogel grafted with at least one polymerizable moiety According to the present invention, "grafted" means a covalent link between the hydrogel and the polymerizable moiety.

The present invention concerns a functionalized hydrogel backbone grafted with at least one polymerizable moiety.

Hydrogel backbones are well known in the art, preferably selected among polysaccharides like alginate, chitosan and agar polymers, proteins like collagen or synthetic polymers capable of forming hydrogels like polyethylene glycols (PEG), polyhydroxyethylmethacrylic acid (pHEMA) and polyacrylic acid.

In preferred embodiments, the hydrogel backbone is selected among the group consisting of carrageenan, chitosan, hyaluronic acid, cellulose, alginate polymers, preferably alginate polymers as described above.

When the hydrogel is an alginate polymer, the polymerizable moiety is preferably grafted on one carboxylic acid group of the alginate polymer.

Polymerizable moieties are known in the art. In a preferred embodiment, the polymerizable moiety is selected among the group consisting of thiophene, aniline and pyrrole groups, preferably a pyrrole group.

The functionalized hydrogel according to the invention advantageously comprises a spacer moiety between the hydrogel backbone and the polymerizable moiety. Such spacer is selected to avoid substantial interference with the polymerization process for the polymerizable moiety. It may be selected among alkylenyl groups, cycloalkylenyl groups, alkenylenyl groups, eventually substituted by one or more substituents.

According to the present invention, alkenyl groups are preferably C1-C6 linear or branched alkenyl groups, including methylenyl, ethylenyl, propylenyl, butylenyl, pentalenyl and hexylenyl radicals. The same definition applies for the alkenylenyl groups, but where it comprises one or more unsaturated bonds.

Cycloalkenyl groups are preferably C3-C6 cycloalkylenyl groups, including cyclopropylenyl, cyclopentylenyl and cyclohexylenyl groups.

Both the hydrogel backbone and the polymerizable moiety may be linked to the spacer on the same carbon atom, or on different carbon atoms.

One or more —CH$_2$— or —CH< groups of the spacer may be replaced by an oxygen, an amino or a carbonyl group.

In preferred embodiments, the polymerizable moiety is grafted to the hydrogel moiety through an amide bond or an ether bond.

Preferred of these functionalized hydrogels according to the invention can be represented by the following formulas (1) and (2)

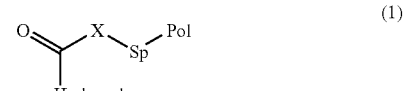

(1)

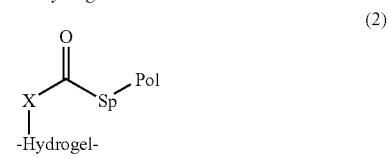

(2)

wherein

Hydrogel is an hydrogel backbone as defined above and below,

Pol is a polymerisation moiety as defined above and below,

Sp is a spacer moiety as defined above and below and

X is an oxygen of an amine group NR1, wherein R1 is selected among H or a C1-C3 alkyl group.

In preferred embodiment, the functionalized hydrogel according to the invention comprises an alginate polymer as hydrogel backbone and a pyrrole moiety as polymerization moiety.

Preferred alginate polymers comprising at least one pyrrole moiety can be represented by the following formula (3)

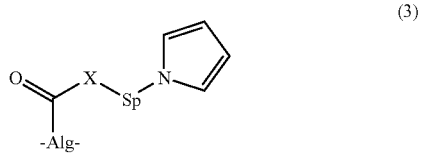

(3)

wherein

X is selected among O or NR1, with R1 being selected among H or a C1 to C3 alkyl group Sp is a spacer moiety selected among alkylenyl groups, cycloalkylenyl groups, alkenylenyl groups, eventually substituted by one or more substituents and Alg is a sugar of the alginate backbone polymer.

Preferred functionalized alginate hydrogels comprising at least one grafted pyrrole moiety of the invention can be represented by the following formula (4)

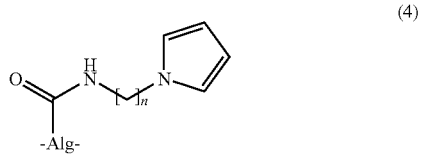

(4)

wherein n is an integer from 1 to 6, preferably 3 and

Alg is a sugar of the alginate backbone polymer.

Alginate hydrogels grafted with pyrrole moieties preferably comprise form 10% to 40% of pyrrole moieties based on the total number of carboxylic acid moieties of the alginate polymer, more preferably about 30% of pyrrole moieties.

To obtain an hydrogel backbone and a polymer are bonded with one or more covalent bonds the polymerizable moiety of the functionalized hydrogen of the present invention is further polymerized.

In situ polymerization of the polymerizable moiety will lead to the formation of the corresponding polymer covalently bond to the hydrogel backbone by one or more covalent bonds, such as a polypyrrole polymer.

Additional properties of the functionalized hydrogel of the present invention are associated with the choice of the polymer being grafted to the hydrogel backbone.

For instance, a polypyrrole polymer will add specific electrochemical properties.

The present invention also concerns a method for the preparation of a functionalized hydrogel as defined above and below, comprising reacting an hydrogel backbone with a polymerizable moiety functionalized to allow the formation of a covalent bond between the hydrogel backbone and the polymerizable moiety.

Formation of a covalent bond between an hydrogel backbone and a polymerization moiety, eventually through a spacer, will depend on the chemical structure of the hydrogel backbone and the polymerizable moiety. Method for such grafting are known in the art.

The method of the invention further comprises polymerizing the functionalized hydrogel of the invention, under conditions suitable for the polymerization of the polymerizable moiety.

Such methods are well known in the art. In a preferred embodiment, polymerization of the polymerizable moiety is done chemically or electro-chemically.

The present invention also concerns a polymer composition comprising functionalized hydrogel as defined above and below preferably in the form of a film or a gel.

The invention also concerns a composition comprising a functionalized hydrogel of the invention or a polymer composition as defined above and below combined with at least a second element selected among cells, proteins, DNA or other molecules. Such composition may be comprised in a biosensor, in a bioreactor or in a pharmaceutical compositions comprising a composition defined above and a pharmaceutically acceptable carrier.

The present invention contemplates the use of pharmaceutical formulations for human medical use which comprise a functionalized hydrogel composition of the present invention as therapeutic ingredients. Such pharmaceutical formulations may include pharmaceutically effective carriers, and optionally, may include other therapeutic ingredients. The carrier or carriers must be pharmaceutically acceptable in the sense that they are compatible with the therapeutic ingredients and are not unduly deleterious to the recipient thereof. The therapeutic ingredient or ingredients are provided in an amount necessary to achieve the desired therapeutic effect.

The term "carrier" refers to a diluent, adjuvant, excipient, or vehicle with which the conjugate is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like.

The composition, if desired, can also contain minor amounts of wetting or emulsifying agents, or pH buffering agents.

The compositions can take the form of solutions, suspensions, emulsion, -tablets, pills, capsules, powders, sustained release formulations and the like. The composition can be formulated as a suppository, with traditional binders and carriers such as triglycerides.

Exemplary means of administration include oral, parenteral, rectal, topical, sublingual, mucosal, nasal, ophthalmic, subcutaneous, intramuscular, intravenous, transdermal, spinal, intrathecal, intra articular, intra arterial, sub arachnoid, bronchial, lymphatic, and intrauterine administration.

Oral formulation can include standard carriers such as pharmaceutical grades of mannitol, lactose, starch, magnesium stearate, sodium saccharine, cellulose, magnesium carbonate, etc.

EXPERIMENTAL SECTION

Figure 1:
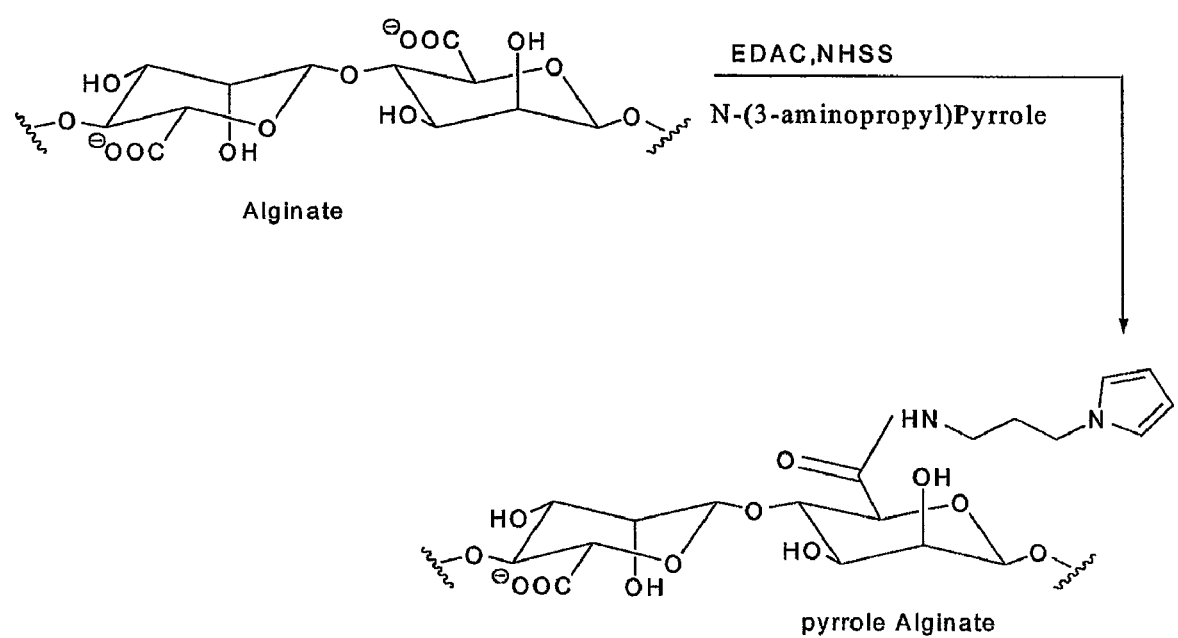
FIG. 1. Pyrrole coupling to alginate via carbodiimide chemistry.

Materials. Chemicals obtained from commercial sources were of analytical grade and were used without further purification. Sodium alginate Protanal LF10/60 (from *Laminaria hyperborea*, 70% G content, average molecular weight of 128 kDa, Viscosity of the 1% (w/v) solution is 40 cP) was supplied by FMC Biopolymer (Norway). 1-(2-Cyanoethyl) pyrrole (C9135-2), lithium aluminum hydride solution (62423), celite (22145), 1-ethyl-[3-(dimethylamino)propyl]-3-ethyl-carbodiimide HCl (EDAC; E-1769), 2-[N-morpholino] ethanesulfonic acid (MES) buffer (M-8250), calcium chloride (C-5426), Polyphenol oxidase (PPO) (EC 1.14.18.1, from mushroom) with an activity of 3620 U mg$^{-1}$ solid, Tris-HCl (T-3253) were purchased from Sigma and Aldrich Co. (USA). N-hydroxysulfosuccinimide (NHSS; 24510), was acquired from Pierce (Rockford, USA). Diethyl ether (5551550) was obtained from Frutarom (Israel), While Lithium perchlorate (194711000) was bought from Acros Organics and Catechol (200-427-5) from ICN Biomedical GmbH.

Synthesis of N-(3-aminopropyl) pyrrole. A solution of 1-(2-cyanoethyl) pyrrole (0.02 mol) in anhydrous ether (15 ml) was added dropwise to a suspension of LiAlH$_4$ (0.05 mol) in anhydrous ether (150 ml) and the mixture was refluxed for 10 h. After cooling, the excess of hydride was destroyed by the successive addition of water (1.7 ml), a solution of 15% (w/v) NaOH (1.7 ml) and water (5.1 ml). The solution was heated to 40° C. for 2 h and filtered on celite before evaporating to dryness. A yellow oil was obtained (Naji, A. Cretin. M, Persin, M, Sarrazin, J. *J. Polmer. Sci.* 2003, 212, 1-11) with a yield of 91.6%. $^1$H-NMR δ (CDCl$_3$): 1.90 (m, 2H, CH$_2$-2); 2.70 (t, 2H, CH$_2$-3); 3.95 (t, 2H, CH$_2$-1); 6.14 (d, 2H, CH-β; 6.65 (d, 2H, CH-α). $^{13}$C-NMR δ (CDCl$_3$): 35.5 (CH$_2$-2); 39.7 (CH$_2$-3). FTIR spectroscopy: the characteristic features of the N-(3-aminopropyl) pyrrole spectrum are a strong sharp peak at 3370 cm$^{-1}$ with a medium shoulder at 3295 cm$^{-1}$ that corresponds to the "free" asymmetrical and symmetrical N—H stretching vibration modes of the aliphatic primary amines.

Preparation of Pyrrole-Conjugated Alginate. The pyrrole-alginate conjugate was prepared by adding 50 mg (0.25 mmol) of N-(3-aminopropyl) pyrrole to a solution of alginate (20 ml solution, 0.25 mmol alginate monomer, 50 mg) in 0.1 M MES buffer, pH 6.0. The reaction mixture was stirred at room temperature for 10 min to facilitate a homogeneous dispersion of the pyrrole reagent in the reaction solution. Then, 13.5 mg g (0.0625 mmol) of NHSS and 24 mg (0.125 mmol) of EDAC were added (ratios of reagents were calculated for a theoretical 50% molar modification of the number of carboxylic groups of alginate). After 3 h at room temperature, the resulting polymer was dialyzed against doubly deionized water using a 6000-8000 MWCO membrane (314 N. River St. USA). The water was changed twice a day for three days, after which time the modified alginate was lyophilized.

Spectroscopic Analysis. For FTIR spectroscopy, polymer samples were prepared as thin films by dissolving 4 mg/ml of the modified alginate into doubly deionized water. The resulting solution was poured into a polystyrene Petri dish and dried in an oven at 50° C. for 24 h to produce a thin transparent polymer film (Sartori, C.; Finch, D. S.; Ralph, B.; Gilding, K. *Polymer* 1997, 38, 43-51). Infrared measurements were performed in transmission mode on a Bruker Equinox 55 infrared spectrometer. The FTIR spectra were averaged over 128 scans at a resolution of 4 cm$^{-1}$.

For $^{13}$C-NMR spectroscopy, samples of modified alginate were dissolved in D$_2$O. $^{13}$C-NMR measurements were performed on a Bruker Advance DNX instrument (500 MHz) utilizing standard Pals programs.

Quantitative Assay of the Extent of Modification of the Alginate. The modification extent of the alginate by N-(3-aminopropyl) pyrrole was evaluated by UV absorbance measurements at 230 nm. Pyrrole-alginate samples were dissolved to produce 0.01% (w/v) alginate solution and measured using a Ultrospec 2100 Pro UV/Visible Spectrophotometer (Biochrom CB4 0FJ, England) at 230 nm. The extent of alginate modification was calculated from the calibration curve obtained by measuring the absorbance of different amounts of N-(3-aminopropyl) pyrrole into 0.01% (w/v) alginate solution. A standard solution of alginate at the concentration of (0.01% w/v) was used as a blank.

Viscosity Measurements. The viscosity of various pyrrole-alginate and non-modified alginate solutions [1.5-3% (w/v) in doubly deionized water] was determined using a Carrimed CLS 50 controlled-stress Rheometer (TA Instruments, UK). The measurements were performed using cone-plate geometry (4 cm/4°).

HPSEC-MALLS Analysis. Molecular weight distributions of the polymers were determined with a multi-angle laser light scattering (MALLS) photometer (DAWN DSP, Wyatt Technology Inc., Santa Barbara, USA), fitted with a K5 flow cell and a He—Ne laser (633 nm). Polymer samples, 3 mg/L, were prepared in a buffer containing 0.02% (w/v) sodium azide and 0.1 M sodium nitrate in 10 mM imidazole solution at pH 7.0. Fractional separations were performed on 100-, 300-, and 1000-Å PSS Suprema separation columns (Polymer Standard Service, Germany). The mobile phase was delivered at ambient temperature at a nominal flow rate of 0.7 mL/min. MALLS and differential refractive index (DRI) detectors were calibrated with filtered HPLC-grade toluene and NaCl solutions, respectively. The MALLS instrument was normalized using standard pululan P-23 (isotropic light scattering). The dn/dc value (specific refractive index increment) for the studied polymers was estimated at 0.155 [mL/g], according to the value reported in the literature for sodium alginate in the presence of NaCl.[18]

Electrochemical instrumentation. All the electrochemical experiments were carried out in a conventional electrochemical cell (Metrohm). A saturated Ag—AgCl-saturated KCl electrode was used as a reference electrode and a Pt wire placed in a separate compartment containing the supporting electrolyte was used as counter electrode. The working electrode was a rotating glassy carbon disk electrode (diameter 5 mm) polished with 2 μm diamond paste (MECAPREX Press PM). The amperometric measurements were performed in 0.1 M Tris-HCl buffer (pH=6.5) using a Tacussel PRG-DL potentiostat and an electrochemical cell thermostated at 20±1° C. The electrochemical control of the amount of enzyme released in the buffer solution was carried out with an Autolab 100 potentiostat.

The electropolymerization process was performed at room temperature by controlled potential oxidation for 20 min at 0.94V in 0.1 M LiClO$_4$ aqueous solution using a potentiostat EG & G Princeton Applied Research 173 equipped with a Model 175 universal programmer in conjunction with a Kipp and Zonen BD 91 XY/t recorder.

Preparation of enzyme electrodes. A 2% (w/v) aqueous solution of alginate or pyrrole-alginate was prepared in 0.1M Tris-HCl buffer (pH=6.5) and stirred overnight at room temperature. The resulting solution was filtered using a 0.22 µm membrane filter to remove microorganisms and contaminants.

A 15 µl mixture of 2% (w/v) alginate or pyrrole-alginate containing 75 µg of polyphenol oxidase (PPO) was spread on the surface of glassy carbon electrodes (diameter 5 mm). The coatings were then gellified by soaking in 0.1M CaCl$_2$ for 15 min. The pyrrole-alginate-PPO electrode was potentiostated at 0.94 V for 10 min to oxidize the pyrrole moieties into polypyrrolic chains inside the gel.

Results and Discussion

Alginate modification. Pyrrole-alginate was prepared in an aqueous phase via carbodiimide chemistry according to the scheme shown in FIG. 1. The aqueous-phase carbodiimide chemistry approach uses a water-soluble carbodiimide (EDAC) that catalyzes the formation of amide bonds between carboxylic acids and amines by activating the carboxylate to form an O-acylisourea intermediate (Khorana, H. G. *Chem. Rev.* 1953, 53, 145-166, DeTar, D. F.; Silverstein, R.; Rogers, F. F., Jr. *J. Am. Chem. Soc.* 1966, 88, 1024-1030). This intermediate is unstable in aqueous solution and undergoes fast hydrolysis. For the procedure to be successful, the active form of alginate carboxyls would have to be more stable than the O-acylisourea derivative. Such a condition could be fulfilled by the so-called "active esters", such as N-hydroxysuccinimidyl esters (NHS) developed for peptide synthesis (Anderson, G. W.; Zimmerman, J. E.; Callahan, F. M. *J. Am. Chem. Soc.* 1964, 86, 1839-1842) or their sulfonated derivatives (Staros, J. V. *Biochemistry* 1982, 21, 3950-3955).

The alginate conjugation chemistry was designed to obtain about 25-35% modification of the molecule to keep about 70% of the carboxylic residues non-modified and available for its cross-linking by calcium. According to our previous study (Polyak, B.; Shimona, G; Marks, R. S. *Biomacromolecules.* 2004, 5, 389-396) and other studies (Rowley, J. A.; Madlambayan, G.; Mooney, D. J. *Biomaterials.* 1999, 20, 45-53) with biotin-alginate modification, the reaction efficiencies were about 70%, therefore a 50% of uronic acid activation chemistry was used for achieving the desired degree of alginate modification. The coupling procedure was performed using the previously described optimal reaction conditions.

Control reactions without the addition of EDAC for activation were run for each experiment. After dialysis, less than 1% of pyrrole moiety was detected by UV spectroscopy, suggesting that the incorporation of pyrrole is not a result of nonspecific interactions or physical entrapment of N-(3-aminopropyl) pyrrole by the polysaccharide.

Spectroscopic Characterization of Pyrrole-Alginate. The pyrrole-alginate product was characterized by FTIR and $^{13}$C-NMR spectroscopy. The characteristic features of the pyrrole-alginate spectrum are strong sharp peaks at 1666 cm$^{-1}$ and at 1560 cm$^{-1}$ which correspond to the amide I band, C=O stretching vibrations, and amide II band, N—H bending vibrations respectively, and a medium-sharp peak at 1282 cm$^{-1}$ (amide II band, interaction between the N—H bending and C—N stretching vibrations) (Silverstein, R. M.; Webster, F. X. *Spectrometric Identification of Organic Compounds, 6th Edition,* 1997).

The $^{13}$C-NMR spectrum confirmed the conjugation of pyrrole to alginate via the formation of an amide bond. In contrast to the chemical shift of the carboxyl group at 174.1 ppm present in the non-modified alginate, the pyrrole-alginate product showed two new chemical shifts, that of 1-amide carbonyl (CONH) at 174 ppm and that of a carbon on the pyrrole ring (CHN) at 121.6 ppm.

Quantification of the pyrrole Content in the Modified Alginate. The extent of modification of alginate by N-(3-aminopropyl) pyrrole was evaluated by UV-visible absorption spectroscopy, which is a useful technique for the detection and quantitative measurements of chromophores that undergo $n \rightarrow \pi^*$ or $\pi \rightarrow \pi^*$ transitions. Because of its sensitivity, UV-visible spectroscopy had been particularly useful in identifying and analyzing "foreign" material in polymers-residual monomer, inhibitors, antioxidants and so on.[33-34] A $\pi \rightarrow \pi^*$ transition occurs in the pyrrole ring present in the pyrrole-alginate conjugate allowing the quantification of the amount of N-(3-aminopropyl) pyrrole by UV-visible absorption spectroscopy at 230 nm. Several samples within a concentration range (50-250 µM) of N-(3-aminopropyl) pyrrole dissolved in alginate solution (0.1 w/v %) were measured by UV absorption at 230 nm. The data collected from UV-absorbance measurements had a very good linear range for the studied N-(3 aminopropyl) pyrrole concentrations ($R^2$=0.99). The extinction coefficient of 2080 M$^{-1}$ cm$^{-1}$ for N-(3 aminopropyl) pyrrole was calculated from the slope of the plotted curve.

The average value of the degree of alginate modification obtained about 30±3% of molar modification for a number of samples related to different synthetic bathes of the pyrrole-alginate conjugate. The relatively low standard deviation indicates a good reproducibility of the modification procedure of the alginate.

Characterization of Molecular Weight Parameters and Viscosity.

Differential molar mass distribution shows how much material (differential weight fraction) is present in any molecular weight interval. Cumulative distribution gives, for each molar mass, the weight fractions of material having molar mass less than the given weight. Thus, the cumulative distribution approaches zero at low molecular weights and unity at high molecular weights. The cumulative distribution is thus particularly useful in determining which molecular weight fractions are contained in the high and low molecular tails of the sample (Tristan, T., Hugo, G. *J. Agric. Food. Chem.* 2000, 48, 5455-5458). The pyrrole-alginate product shows a clear shift to higher molecular weights in both distribution presentations.

This result of the light scattering provides a method for determining absolute molecular weight and size distribution (Debye, P. J. W. *J. Appl. Phys.* 1944, 15, 338-342), which implies that pyrrole, is probably distributed homogeneously on the alginate backbone. The weight-average molecular weight ($M_w$) for pyrrole-alginate (30±3% molar modification) was measured as 370-390 kDa ($M_w/M_n$=3.03-3.4) by means of SEC. This value represents an increase from the initial $M_w$ of alginate ($M_w$=128 kDa, $M_w/M_n$=1.14). The ratio $M_w/M_n$ is a measure of the dispersivity of the polymer chains. The meaning of the wide ratio of $M_w/M_n$ for pyrrole-alginate and alginate is that we have poly-dispersed polymers.

The viscosity of pyrrole-alginate solutions at various concentrations showed that the viscosities were higher than that of the original alginate solution (Table 1).

This finding reflects the increase of the molecular weight of the modified alginate relative to the original alginate as well as the increase in the hydrophobic character of the modified alginate due to the organic pyrrole moieties.

TABLE 1

Viscosity of 30 ± 3% Modified pyrrole-Alginate and Original Alginate Measured at a Shear Rate of 100 s$^{-1}$

| Polymer concentration (% w/v) | Viscosity (cp) [a] | |
| --- | --- | --- |
| | Pyrrole-alginate | Original alginate |
| 1.5 | 309 | 46.25 |
| 2.0 | 900.9 | 105.2 |
| 2.5 | 957.9 | 196.4 |
| 3.0 | 1977 | 605.7 |

[a] Data represent the means of three independent experiments with maximal SD of 5%

The carboxylic group interactions in the alginate monomer increase the steric hindrance affecting the distance between the chains of the polymers, which lead to the reduction in the shear forces and viscosity reduction of the solution of the regular alginate compared to the pyrrole-alginate solutions, where the chemical modification of the carboxylic group of the monomer by N-(3-aminopropyl) pyrrole leads to less interactions, higher stability of the hydrogel and high viscosity.

Biosensor Construction.

To characterize the impact of the in situ-electrogenerated polypyrrole skeleton on the retention properties of the alginate gel, the phenomenon of enzyme release or loss was investigated for regular alginate and polypyrrole-alginate. Polyphenol oxidase (PPO) which catalyzes the oxidation of phenols and o-diphenols with a concomitant consumption of oxygen was chosen an enzyme model. The two biosensor configurations: alginate-PPO and polypyrrole-alginate-PPO were soaked separately in 0.1 M Tris-HCl buffer (pH=6.5) for 15 min at room temperature. The enzyme leakage in solution was estimated amperometrically from their activity towards the oxidation of catechol. A bare glassy carbon electrode was thus potentiostated at −0.2V vs Ag/AgCl and the reduction current of the enzymatically-generated quinone was recorded after the addition of catechol (2 mM).

The comparison of the linear part of the slope of current vs. time curve with the slope obtained using the same conditions in presence of free PPO molecules indicated that 20% (15 µg) and 60% (45 µg) of the initial entrapped PPO molecules were lost from polypyrrole-alginate and alginate coatings, respectively. This unambiguously demonstrates the beneficial effect brought by the polymerization of the pyrrole moieties chemically grafted on alginate gel on the enzyme retention properties of the resulting gel.

In-situ electrogenerated polypyrrole seems to act as an additional polymeric binder that reinforces the stability of the alginate gel. Moreover, the analytical characteristics of polypyrrole-alginate-PPO and alginate-PPO electrodes for the determination of catechol were investigated by potentiostating both biosensors at −0.2V in order to reduce the quinone enzymatically generated within the gels. The steady-state current-time response to catechol injections indicates short response time (20 s) for both biosensor configurations illustrating the excellent permeabilities of these alginate gels. The resulting calibration curves led to sensitivity value (determined as the slope of the initial part of the calibration curve) to catechol of 350 and 80 µAM$^{-1}$ cm$^{-2}$ for polypyrrole-alginate and alginate biosensors respectively. In addition, the maximum current value ($I_{max}$) for polypyrrole-alginate biosensor (42 µA cm$^{-2}$) was 4.4 times higher than that recorded for alginate biosensor (9.5 µA cm$^{-2}$). It should be noted that $I_{max}$ is directly related to the available amount of immobilized enzyme. These results corroborate the major role played by the in situ generated polypyrrole for the retention of immobilized enzyme molecules with preservation of their activity.

Electrode Functionalization

For the functionalization of the electrode, 3 µl of 2% (w/v) aqueous solution of alginate or pyrrole-alginate was spread on the electrode surface (carbon disk, diameter 5 mm) and left to react with a drop of 0.1 M CaCl$_2$ for 5 min[16,17]. In order to demonstrate the possibility to electrochemically polymerize the pyrrole moieties grafted on the alginate skeleton in its gel form and the influence of the resulting polymer on the physical properties of the alginate coating, the mass transfer through different alginate gels was examined by cyclic voltammetry. The permeation of ferrocene dicarboxilic (2 mM) in 0.1M Tris-HCl (pH=7) through alginate and pyrrole-alginate coatings was thus illustrated by its one-electron oxidation at the underlying electrode surface. The presence of these gel coatings led to a similar and marked decrease in the intensity of the reversible peak system compared to the signal recorded at a bare electrode. Both gels were then oxidized by controlled potential electrolysis in H$_2$O+0.1 M LiClO$_4$ for 10 min at 0.93 V versus a saturated Ag—AgCl—KCl electrode (Ag/AgCl). The expected pyrrole-alginate polymerization was indeed highlighted via the strong decrease (−70%) in the intensity of the oxidation peak of ferrocene derivative compared to its initial value (34 µA) before the electropolymerization process. This increase in diffusional resistance reflects the formation of polymerized chains within the gel structure. In contrast, the cyclic voltammogram relative to the oxidized regular alginate showed an increase in current intensity from 32 µA to 42 µA. This may reflect a partial loss of alginate gel into the solution during the polymerization step illustrating thus the unstability of the coating.

In order to confirm the existence of a polypyrrole network in the case of the oxidized pyrrole-alginate, which would be capable of reinforcing the gel stability, a polymer elimination step obtained by the organic washing and chemical destabilization (soaking for 10 min in stirred 95% (v/v) ethanol solution followed by 10 min in 0.1 M phosphate buffer (pH=7)) was carried out to remove the alginate coating from the electrode surface. In the case of polypyrrole-alginate, an increase in the oxidation peak was observed reaching 50% of the intensity value recorded at a bare electrode whereas an electrochemical signal identical to that displayed at a bare electrode, was recorded for regular alginate. This comparison clearly demonstrates the beneficial effect brought by the electropolymerization process on the stability of the alginate coating. In particular, the presence of the polymerized network inside the gel seems to counterbalance the destructive effect of phosphate ions that normally would induce a displacement of the gelling agent CaCl$_2$.

In order to corroborate the presence of polypyrrolic chains within the alginate gel, the permeabilities of alginate and polypyrrole-alginate coatings were determined by rotating-disk electrode experiments (RDE) that were carried out at different rotation rates in the presence of hydroquinone (1 mM) in 0.1M Tris-HCl (pH=7). The large difference in permeability values, respectively 3.65×10$^{-1}$ and 2.7×10$^{-2}$ cm$^{-2}$ s$^{-1}$ for alginate and polypyrrole-alginate, reflects unambiguously the steric hindrances due to the <<in situ>> generated polypyrrolic chains.

Besides the stabilization of alginate coating, another useful property would be the possibility of firmly entrapping proteins such as in the fabrication of enzyme sensors. The ability of polypyrrole-alginate to retain proteins was investigated with glucose oxidase (GOx) (chosen as a model) for its ability to catalyse the production of electroactive $H_2O_2$ in the presence of glucose and oxygen. The release of GOx molecules can be evaluated amperometrically through the oxidation of the enzymatically generated $H_2O_2$. For this purpose, two separate types of enzyme coatings were prepared by spreading on the electrode surface (diameter 5 mm) a mixture containing 15 μl of either alginate or pyrrole-alginate and GOx (75 μg) followed by the incubation with $CaCl_2$ (0.1 M) for 5 min. As previously described, the polypyrrole-alginate-GOx electrode was obtained by electropolymerization at 0.93 V (Aubrée-Lecat, C. Hervagault, A. Delacour, P. Beaude, C. Bourdillon and M. H. Remy, *Anal. Biochem.* 1989, 178, 427).

The resulting electrodes were soaked in 2 ml of stirred 0.1M Tris-HCl buffer (pH 7) solution for one hour. The release of GOx molecules with time was periodically followed by sampling the exudates by electrochemical determination Aliquots (100 μl) after 5, 10, 30, 45 and 60 min were injected into a phosphate buffer (10 ml, pH 7) containing glucose (50 mM) and the increase in $H_2O_2$ concentration was recorded through its oxidation at a platinum electrode potentiostated at 0.6 V. The linear part of the slope of anodic current vs. time curve was compared with that obtained using the same conditions in presence of a known amount of Gox.

It appears that the enzyme release decreases with time reaching a stable value after one hour. Thus, 40% (30 μg) and 12% (9 μg) of the initially entrapped amount of GOx molecules were lost from alginate and polypyrroles-alginate films respectively. This clearly demonstrates a better retention of enzyme molecules within polypyrrole-alginate hydrogels thanks to the additional polymeric cross-linking.

Finally, amperometric glucose biosensors were designed by incorporating GOx (15 μg) into alginate or polypyrrole-alginate hydrogel coatings (3 μl). The resulting enzyme electrodes were potentiostated at 0.6 V and their amperometric response to glucose was recorded in 0.1M Tris-HCl buffer (pH=7). Amperometric measurements were performed with a electrochemical cell thermostated at 25° C. under stirred conditions in 10 ml (0.1 M Tris-HCl, pH 7) and stock solutions of glucose were mutarotated at room temperature for 24 h before use.

The calibration curves representing the biosensor response as a function of glucose concentration, indicate for both configurations that the current increased linearly with glucose concentration, while a pseudo plateau was reached at higher concentrations. As expected, the comparison of the biosensor performance in terms of maximum current ($I_{max}$) and sensitivity values shows that the polypyrrole-alginate coating provided higher $I_{max}$ (1.11 μA) and sensitivity (122 μAM$^{-1}$) values than those obtained with the alginate electrode, namely 0.62 μA and 34 μAM$^{-1}$. This confirms that the polymerization process which induced a higher retention degree of GOx molecules, contributes to the improvement of the biosensor performance.

The influence of the amount of electrodeposited polypyrrole-alginate-GOx coating on the analytical characteristics of the enzyme electrode was also investigated. After the successive gellification and electropolymerization processes of 3 and 15 μl of pyrrole-alginate-GOx mixtures, the analytical performances of the biosensors were determined. Both biosensors presented similar kinetic behaviour illustrated by an identical value of Michaelis-Menten constant (12 mM) and a fast response time (4 s).

However, higher $I_{max}$ and sensitivity values (4.17 μA and 600 μAM$^{-1}$, respectively) were obtained with the polypyrrole-alginate biosensor corresponding to 15 μl. It should be noted that a similar ratio (4-5) was calculated from the comparison of the $I_{max}$ and sensitivity values. This factor is in good accordance with the ratio (5) of the deposited amounts of GOx, illustrating thus, the reproducibility of the improvement effect due to the polypyrrole network.

The results described herein demonstrate, for the first time, the electrochemical polymerizing abilities of an alginate polymer pre-deposited under its gel form on an electrode surface and its usefulness in reinforcing the mechanical and chemical properties of the alginate gel. The polypyrrole-alginate may thus constitute an attractive electrogenerated coating for the immobilization of enzymes.

The invention claimed is:

1. A functionalized hydrogel backbone grafted with at least one polymerizable moiety, wherein the hydrogel is an alginate polymer, and the polymerizable moiety is grafted on one carboxylic acid group of the alginate polymer comprising from 10% to 40% of pyrrole moieties based on the total number of carboxylic acid moieties of the alginate polymer.

2. The functionalized hydrogel of claim 1, wherein the polymer comprises a spacer moiety between the hydrogel backbone and the polymerizable moiety.

3. The functionalized hydrogel of claim 2, wherein the spacer moiety is selected from the group consisting of alkylenyl groups, cycloalkylenyl groups, and alkenylenyl groups.

4. The functionalized hydrogel of claim 3, wherein the alkylenyl groups, cycloalkylenyl groups, or alkenylenyl groups are substituted by one or more substituents.

5. The functionalized hydrogel of claim 1, wherein the polymerizable moiety is grafted through an amide bond or an ether bond.

6. A functionalized polymer, represented by the following formula:

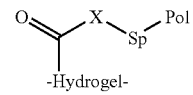

wherein
Hydrogel is an alginate polymer,
Pol is a polymerization moiety,
Sp is a spacer moiety and
X is an oxygen or an amine group NR1, wherein R1 is selected among H or a C1-C3 alkyl group wherein the polymer comprises from 10% to 40% of pyrrole moieties based on the total number of carboxylic acid moieties of the alginate polymer.

7. The functionalized polymer of claim 6, wherein the polymerization moiety is a pyrrole moiety.

8. The functionalized polymer of claim 6, wherein the alginate polymer comprises at least one pyrrole moiety of the following formula:

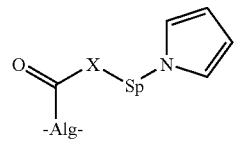

wherein
X is O or NR1, with R1 being H or a C1 to C3 alkyl group,
Sp is a spacer moiety selected from the group consisting of alkylenyl groups, cycloalkylenyl groups, and alkenylenyl groups, and
Alg is a sugar of the alginate polymer.

9. The functionalized polymer of claim 8, wherein the alkylenyl groups, cycloalkylenyl groups, or alkenylenyl groups are substituted by one or more substituents.

10. The functionalized polymer of claim 6, comprising at least one grafted pyrrole moiety of the following formula:

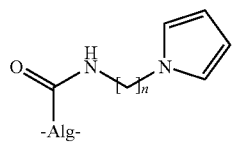

wherein
n is an integer from 1 to 6, and
Alg is a sugar of the alginate backbone polymer.

11. The functionalized polymer of claim 10, wherein n is 3.

12. The functionalized polymer of claim 6, wherein the polymer comprises about 30% of pyrrole moieties.

13. The functionalized polymer of claim 6, wherein the polymerizable moiety is grafted on one carboxylic acid group of the alginate polymer.

14. The functionalized polymer of claim 6, wherein the spacer moiety is selected from the group consisting of alkylenyl groups, cycloalkylenyl groups, and alkenylenyl groups.

15. The functionalized polymer of claim 14, wherein the alkylenyl groups, cycloalkylenyl groups, or alkenylenyl groups are substituted by one or more substituents.

16. The functionalized hydrogel of claim 1, wherein the polymerizable moiety is further polymerized.

17. The functionalized hydrogel of claim 16, comprising a hydrogel backbone and a polymer, wherein the hydrogel backbone and the polymer are bonded with one or more covalent bonds.

18. A method for the preparation of a functionalized hydrogel of claim 16, comprising polymerizing the functionalized hydrogel, under conditions suitable for the polymerization of the polymerizable moiety.

19. The method of claim 18, wherein polymerization of the polymerizable moiety is done chemically or electro-chemically.

20. A polymer composition comprising the functionalized hydrogel of claim 1.

21. The polymer composition of claim 20, wherein the composition is in the form of a film or a gel.

22. A biosensor comprising the polymer composition of claim 21.

23. A composition comprising the functionalized hydrogel of claim 1 or the polymer composition of claim 20, combined with at least a second element selected from the group consisting of cells, proteins, DNA or other molecules.

24. A pharmaceutical composition comprising the composition of claim 23 and a pharmaceutically acceptable carrier.

25. A biosensor comprising the composition of claim 23.

26. A method for the preparation of a functionalized hydrogel claim 1, comprising reacting a hydrogel backbone with a polymerizable moiety functionalized to allow the formation of a covalent bond between the hydrogel backbone and the polymerizable moiety.

27. A functionalized hydrogel backbone grafted with at least one polymerizable moiety wherein the hydrogel is an alginate polymer and the polymerizable moiety is grafted on one carboxylic acid group of the alginate polymer, wherein the hydrogel comprises calcium ions and wherein the polymer comprises from 10% to 40% of pyrrole moieties based on the total number of carboxylic acid moieties of the alginate polymer.

28. A functionalized hydrogel backbone grafted with at least one polymerizable moiety wherein the hydrogel is an alginate polymer and the polymerizable moiety is grafted on one carboxylic acid group of the alginate polymer allowing formation of a composite layer of alginate crosslinked with polypyrrole wherein the polymer comprises from 10% to 40% of pyrrole moieties based on the total number of carboxylic acid moieties of the alginate polymer.

29. A functionalized hydrogel backbone grafted with at least one polymerizable moiety wherein the hydrogel is an alginate polymer and the polymerizable moiety is grafted on one carboxylic acid group of the alginate polymer, wherein the polymerizable moiety is further polymerized without the use of other polymerizable monomers wherein the polymer comprises from 10% to 40% of pyrrole moieties based on the total number of carboxylic acid moieties of the alginate polymer.

* * * * *